United States Patent
Harrer et al.

(10) Patent No.: US 10,765,332 B2
(45) Date of Patent: Sep. 8, 2020

(54) DETECTION OF THE HEARTBEAT IN CRANIAL ACCELEROMETER DATA USING INDEPENDENT COMPONENT ANALYSIS

(71) Applicant: Brainlab AG, Munich (DE)

(72) Inventors: Christian Harrer, San Francisco, CA (US); Stephan Mittermeyer, Los Altos, CA (US); Bálint Varkuti, Munich (DE)

(73) Assignee: BRAINLAB AG, Munich (DE)

( * ) Notice: Subject to any disclaimer, the term of this patent is extended or adjusted under 35 U.S.C. 154(b) by 499 days.

(21) Appl. No.: 15/569,535

(22) PCT Filed: Apr. 29, 2015

(86) PCT No.: PCT/EP2015/059279
§ 371 (c)(1),
(2) Date: Oct. 26, 2017

(87) PCT Pub. No.: WO2016/173639
PCT Pub. Date: Nov. 3, 2016

(65) Prior Publication Data
US 2018/0296107 A1    Oct. 18, 2018

(51) Int. Cl.
*A61B 5/00* (2006.01)
*A61B 5/024* (2006.01)
(Continued)

(52) U.S. Cl.
CPC ........ *A61B 5/02438* (2013.01); *A61B 5/0245* (2013.01); *A61B 5/02416* (2013.01);
(Continued)

(58) Field of Classification Search
CPC ......... A61B 5/024; A61B 5/00; A61B 5/0245; A61B 5/7203; A61B 5/7221;
(Continued)

(56) References Cited

U.S. PATENT DOCUMENTS

| 8,905,932 B2 | 12/2014 | Lovoi et al. |
| 2005/0027416 A1 | 2/2005 | Basir et al. |

(Continued)

FOREIGN PATENT DOCUMENTS

| EP | 0277091 A2 | 7/2009 |
| EP | 2430975 A1 | 3/2012 |

(Continued)

OTHER PUBLICATIONS

Tsouri, et al., Constrained independent component analysis approach to nonobtrusive pulse rate measurements. Journal of Biomedical Optics 17(7), 077011 (Jul. 2012). (Year: 2012).*

(Continued)

*Primary Examiner* — Eric J Messersmith
(74) *Attorney, Agent, or Firm* — Tucker Ellis LLP

(57) ABSTRACT

The invention relates to a computer-implemented medical data processing method for determining a heartbeat signal describing the heartbeat of a patient in the time domain, the method comprising executing, on a processor of a computer, steps of: a) acquiring, at the processor, acceleration measurement data describing an acceleration in the time domain of an anatomical body part measured on an external surface of the anatomical body part; b) determining, by the processor, component analysis data describing a result of an independent component analysis in the time domain of the acceleration measurement data; c) acquiring, at the processor, heartbeat template data describing template shapes of heartbeat in the time domain; d) determining, by the processor and based on the component analysis data and the heartbeat template data, recurrent shape data describing a recurrence of certain signal shapes in the component analysis data; e) determining, based on the recurrent shape data, heartbeat signal data describing a time series of the heartbeat.

20 Claims, 5 Drawing Sheets

(51) Int. Cl.
*A61B 5/0452* (2006.01)
*A61B 5/0245* (2006.01)

(52) U.S. Cl.
CPC ........ *A61B 5/04525* (2013.01); *A61B 5/4064* (2013.01); *A61B 5/6803* (2013.01); *A61B 5/6814* (2013.01); *A61B 5/7203* (2013.01); *A61B 5/7221* (2013.01); *A61B 5/7246* (2013.01); *A61B 5/7257* (2013.01); *A61B 2562/0219* (2013.01)

(58) Field of Classification Search
CPC .............. A61B 5/7246; A61B 5/02438; A61B 5/04525; A61B 5/6803; A61B 5/6814; A61B 5/7257; A61B 5/02416; A61B 5/4064; A61B 2562/0219
See application file for complete search history.

(56) References Cited

U.S. PATENT DOCUMENTS

| | | |
|---|---|---|
| 2006/0224074 A1 | 10/2006 | Kazushige et al. |
| 2009/0177101 A1* | 7/2009 | Hersh ................ A61B 5/04017 600/511 |
| 2011/0066041 A1* | 3/2011 | Pandia ................... A61B 5/029 600/484 |
| 2012/0232418 A1* | 9/2012 | Kimura .............. A61B 5/02411 600/528 |
| 2013/0235323 A1 | 9/2013 | Sotzing et al. |
| 2014/0275879 A1 | 9/2014 | Addison et al. |
| 2014/0288543 A1 | 9/2014 | Liu et al. |

FOREIGN PATENT DOCUMENTS

| | | |
|---|---|---|
| WO | 2013063879 A1 | 5/2013 |
| WO | 2015002933 A1 | 1/2015 |

OTHER PUBLICATIONS

Shafiq, G., Veluvolu, K., Surface Chest Motion Decomposition for Cardiovascular Monitoring. Sci Rep 4, 5093 (2015) (Year: 2015).*

European Patent Office, International Search Report and Written Opinion from corresponding PCT/2015/059279, pp. 1-9, dated Jan. 7, 2016.

Jung et al., "Removing electroencephalographic artifacts by blind source separation", Psychophysiology, 37, Published 2000, pp. 163-178, Cambridge University Press. Printed in the USA.

* cited by examiner ized medical data processing method for determining a heartbeat signal describing the heartbeat of a patient in the time domain, a corresponding computer program and a non-transitory computer-readable storage medium storing that program, a computer running that program or comprising that program storage medium, and a system for determining a heartbeat signal describing the heartbeat of a patient comprising that computer and a plurality of acceleration sensors which are operatively coupled to the computer.

DETECTION OF THE HEARTBEAT IN CRANIAL ACCELEROMETER DATA USING INDEPENDENT COMPONENT ANALYSIS

RELATED APPLICATION DATA

This application is a national phase application of International Application No. PCT/EP2015/059279 filed Apr. 29, 2015 and published in the English language.

The present invention is directed to a computer-implemented medical data processing method for determining computer-implemented medical data processing method for determining a heartbeat signal describing the heartbeat of a patient in the time domain, a corresponding computer program and a non-transitory computer-readable storage medium storing that program, a computer running that program or comprising that program storage medium, and a system for determining a heartbeat signal describing the heartbeat of a patient comprising that computer and a plurality of acceleration sensors which are operatively coupled to the computer.

For many medical applications, it is desirable to reliably determine the geometry (specifically, positions) of the human vasculature in the brain preferably in a non-invasive manner. This may be important e.g. for conducting neurosurgical or radiotherapeutic/radiosurgical procedures as well as diagnosis of clinical indications which are related to changes of the physical properties of the brain matter itself (such as Alzheimer's disease or concussions), during which damage to vessels should be avoided. Known approaches include using vibrations due to the blood pulse in cranial vessels which can be measured on the surface of the head as mechanical signal from which information about the physical (elastic) properties of the interior of the head and hence the vessel structure may be deduced. The physical properties can be deduced by applying tomography algorithms known from the theory of elastic waves. However, the pulse signal will be mixed with noise which is generally difficult to be separated from the pulse signal so that reliable determination of the elastic properties can be hampered.

The state of the art employs a comparative measurement of the pulse signal for detection of the pulse signal in the measured vibrations. For example, the Nautilus BrainPulse 1100 device supplied by Jan Medical Inc. relies on a photoplethysmography (PPG) sensor for detecting the patient's heartbeat. This heartrate signal, used in combination with the acceleration data describing the vibrations, is used for further analysis and diagnosis procedures. However, the application of a PPG sensor (or any other modality) for this purpose has some significant drawbacks:

Adding an additional sensor adds to the complexity of the system, increasing maintenance and production cost.

Experimenting with different positions for the PPG sensor (for example on the forehead or the earlobe) has shown that it is often hard to obtain the heartbeat signal by PPG. Especially when obtaining recordings of subjects with very dark skin or a low skin perfusion, it often takes a long time to reach a satisfactory signal quality.

Even if the heartbeat signal can be obtained by PPG, this is not necessarily in synchronization with the actual blood pulse in the brain, there might be an offset between the actual pulse and the PPG peak, since the PPG signal is only specific to the distinct point where the sensor is applied. Since synchronicity of the heartrate signal with the acceleration data is extremely important for further analysis, like averaging acceleration data over a multitude of heartbeats, this issue might be detrimental to the overall signal analysis process.

Using an ECG (EKG) signal to monitor the heartbeat (which has been done in the past) adds even more complexity to the system, and increases the synchronization problems, since there is a clear delay between the electrical signal of a heartbeat and the arrival of the heartbeat-triggered blood pulse at the cranial vasculature.

A combination of ECG and PPG, or the introduction of another additional modality for obtaining the heart-rate does not change these issues and further reduces usability of the system in daily clinical practice.

An object of the invention therefore is to provide a method for reliable non-invasive detection of the heartbeat (the blood pulse) in the head which specifically allows for an efficient separation of the heartbeat signal from noise.

Aspects of the present invention, examples and exemplary steps and their embodiments are disclosed in the following. Different advantageous features can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method encompasses determining a heartbeat signal from a measurement of vibrations on the surface of the head which are analysed into independent components by application of a Fast Independent Component Analysis (FastICA) algorithm. The result is compared to a predetermined library of wave forms for heartbeat signals, the most similar signals are then picked and combined to determine the measured heartbeat signal. The measured heartbeat signal can be compared to a comparative measurement conducted in parallel e.g. using a PPG sensor to check whether the measurement is valid.

GENERAL DESCRIPTION OF THE PRESENT INVENTION

In this section, a description of the general features of the present invention is given for example by referring to possible embodiments of the invention.

In general, the invention reaches the aforementioned object by providing a new method for extracting the heartbeat signal directly from the acceleration sensor data, rendering any additional modality for detecting the subject's heartbeat superfluous or, even if such a sensor is still present, provides a valuable means for determining the temporal offset between the actual heartbeat and the arrival of the distinctive blood pulse in the cranial vasculature.

In one aspect, the invention is directed to a computer-implemented medical data processing method for determining computer-implemented medical data processing method for determining a heartbeat signal describing the heartbeat of a patient in the time domain.

The method comprises the following exemplary steps which are (all) constituted to be executed by a computer (for example, a specific module such as a software module can be provided which contains code which, when executed on the electronic processor of the computer, provides the data processing functionality of the respective method step). The method steps are executed for example by the processor of such a computer, for example by acquiring data sets at the processor and determining data sets by the processor.

For example, acceleration measurement data is acquired which describes an acceleration in the time domain of an anatomical body part measured on an external surface of the anatomical body part. Specifically, the acceleration measurement data describes a time series of acceleration signals due to the heartbeat/pulse-induced vibration of the surface of an anatomical body part such as the head or any other anatomical body part on the surface of which a heartbeat-induced vibration can be measured. In order to measure the acceleration signals, a system for determining a heartbeat signal is used which comprises a measurement array having at least a plurality of acceleration sensors disposable on a surface of the anatomical body part of the patient. The acceleration sensors configured to generate acceleration signals for measuring an acceleration of the surface. The system also comprises a computer which is operatively coupled to the acceleration sensors and configured to receive information corresponding to the acceleration signals from the acceleration sensors and to acquire the acceleration measurement data based on that information. The computer may also conduct the remaining data processing in accordance with the disclosed method. The system also constitutes an aspect of the invention.

For use on the head, the measurement array has three basic components: a headset with a detachable cable (the headset comprising the plurality of acceleration sensors) and a data collector which is coupled to the computer. The measurement array collects vibration signals due to the heartbeat/pulse-induced vibration of the head and writes them as the acceleration measurement data to brain oscillation-recording files. The files are stored by the computer on a for example non-transitory computer-readable medium such as a hard disk drive. The vibration signals are derived by sensing, using the acceleration sensors placed on the surface of the head) small signals created by the effect of pulse-induced brain oscillations on the skull. The system senses these signals on the skull, via sensitive passive sensors (accelerometers as an embodiment of the acceleration sensors), which are an integral part of the headset. The accelerometers convert the skull motion to very low-level analogue electronic signals. The data collector then digitizes the analogue signals. The digitized signals are passed to the computer where the software creates and stores a data file comprising the corresponding acceleration measurement data. Every heartbeat stimulates the motion of the skull in a repeating oscillatory pattern. The motion is dependent on the size, shape, structure and rate of blood flow in and adjacent to the vascular system. This motion travels through the brain and other material inside the head and exerts minute forces on the skull that the acceleration sensors measure. The motion is expressed in terms of acceleration, velocity, and displacement. Inside the head, the motion is so small that velocity and displacement cannot be accurately detected. However, the acceleration of the skull in response to the brain oscillation can be detected with very sensitive accelerometers.

The headset part contains for example six accelerometers that are placed in key locations where the response of the skull to the acceleration of the blood flow is best detected. The accelerometers detect the brain oscillation patterns taking place inside the head and transform them into small analogue electronic signals for processing by the data collector.

Algorithms for data analysis of data acquired with the system can be synchronised to the precise timing of the heartbeat-induced surges (vibrations) for proper processing of the electronic signal. This is currently done with a portion of the headset that provides a "gating" signal. The gating signal is created with a photoplethysmography (PPG) sensor which is also integral to the headset and from which heart-rate information can be derived. These heartbeat signals are then used to mark the acceleration signals with start and end points. The invention eliminates the need for the PPG sensor by deriving the gating signal from the accelerometer signal itself.

The accelerometers provide analogue electronic signals that are in direct proportion to the acceleration by being in contact with the skin and/or hair on the head of the patient. The data collector utilizing the "mark" provided by the gate signals converts these small electronic signals into digital format. The resulting digital data sets are then stored in a digital file by the computer software. The signal output from all accelerometers as well as a top-placed omnidirectional-sound pressure level sensor (SPL) (for the purpose of ambient noise identification) and the PPG sensor can be combined in a single detachable cable for connection to the headset. The cable is attached to the headset once the headset has been satisfactorily seated on the subject's head.

For example, component analysis data is then determined which describes a result (or the for example unique result) of an independent component analysis (specifically, in the time domain) of the acceleration measurement data, which is done as an exemplary part of the disclosed method by running an independent component analysis (ICA) algorithm on the acceleration measurement data such as Fast Independent Component Analysis (FastICA).

The method may also comprise the following exemplary steps:
  determining whether a real-time independent component analysis on the acceleration measurement data is possible, and
  if it is determined that the real-time independent component analysis is possible,
    determining the component analysis data from a stream of the acceleration measurement data; and
  if it is determined that the real-time independent component analysis is not possible,
    buffering (e.g. storing in a buffer memory) the acceleration measurement data and
    determining the component analysis data by conducting the independent component analysis on at least one batch of the buffered acceleration measurement data.

Independent component analysis (ICA) is a method of blind source signal separation. It allows for extraction of unknown source signals, which are linearly mixed together. ICA assumes that the signals acquired by n sensors to be a linear combination of m independent input signals (e.g. n microphones in a room where m people are talking simultaneously). In terms of ICA, 'independent' means that the signal components resulting from the ICA have a maximal statistical independence. In the above example, ICA yields reconstructions of the voices of the m people as output components.

The disclosed method applies ICA on cranial acceleration data (the acceleration measurement data) acquired by several acceleration sensors applied at different positions of a subject's head. After or during an accelerometer measurement session with a suitable hardware setup such as the above-described system, the following steps are performed.

A recording segment of a suitable length (spanning a multitude of heartbeats) is obtained as the acceleration measurement data from sensor signals of all available acceleration sensors or an arbitrary subgroup (however, the maximum amount of independent components is limited by the number of input signals).

In the disclosed method, the input matrix $X \in \mathbb{R}^{n \times m}$ contains the acceleration measurement data acquired by m acceleration sensors, each column $$x_i = (x_{i1}, \ldots, x_{in})^T, i \in \{1, \ldots, m\} \quad (1)$$

of the matrix X representing a time series of n samples per acceleration sensor as 32-bit floating point numbers. The sampling rate r is a parameter of the measurement hardware, and is typically 2560 samples/s and the number of sensors typically is n=6. The input signals may be processed in the raw state or undergo a certain preprocessing (de-noising, filtering etc). The disclosed method hence includes for example preprocessing the acceleration measurement data for at least one of noise reduction, low pass filtering and high pass filtering. Specifically, the acceleration measurement data is normalized and a whitening filter is applied to facilitate further processing but the preprocessing is not limited to these procedures, nor are they mandatory.

In the case of cranial accelerometry, the data in each sensor reading is considered to be resulting from a mixture (specifically for ICA it is a linear combination of source signals)

$$s_i = (s_{i1}, \ldots, s_{in})^T, i \in \{1, \ldots, m\} \quad (2)$$

caused by specific events, one of them being the heartbeat. These source signals are the columns of the matrix $S \in \mathbb{R}^{n \times m}$ where a mixing matrix $M \in \mathbb{R}^{n \times n}$ establishes the following linear transformation:

$$X = M \cdot S \quad (3)$$

The unknown parameters M and S are obtained by applying the FastICA algorithm as a specific version of an ICA algorithm.

While other algorithms like Principal Component Analysis (PCA) project the data on an orthogonal base, the objective of Independent Component Analysis (ICA) methods, including the FastICA algorithm, is for the obtained components to be of maximal statistical independence. This guarantees that redundant information contained in the single components (the $s_i$) is minimized.

In other words, the sources of the measured acceleration timelines are assumed to be independent, hence the joint probability distribution function P is the product of the densities of all sources:

$$P(S) = \Pi p(s_i) \quad (4)$$

Mathematically, this term is minimized when the single factors of this product are the least Gaussian, e.g. their distribution differs as much as possible from a Gaussian distribution.

The FastICA uses an iterative approach, trying to minimize Gaussian character of the single source components by using higher order moments of distributions like the kurtosis as optimization cost function. For a random variable x given $E\{\}$ as the expectation operator, and $$\mu_x = E\{x\} = \int_{-\infty}^{\infty} p_x(x) dx \quad (5)$$

$$\sigma_x^2 = E\{(x - \mu_x)^2\} = \int_{-\infty}^{\infty} (x - \mu_x)^2 p_x(x) dx \quad (6)$$

The kurtosis is defined as:

$$\kappa = \frac{E\{(x - \mu_x)^4\}}{\sigma^4} \quad (7)$$

In the disclosed method, the independent component channels S are extracted by the FastICA algorithm.

The ICA calculations may be run on hardware chips embedded within the system, including Field Programmable Gate Array (FPGA) chip types which have connections that can be fitted with a certain plasticity, to adapt to optimization procedures. This can be utilized to tune the analysis process to the patient's specific signal profile while providing a hardware-speed calculation and constitutes a personalized medicine application. The calculation hence can be implemented as a discrete (numerical) representation of the above equations (1) to (7).

The heartbeat signal can be extracted from the independent component channels by scanning for recurring periodic features showing up in single independent components or any arbitrary combination of independent components, up to all available components simultaneously. In this context, a feature can be defined as a qualitatively similar shape or pattern such as a distinctive waveform, recurring signal section with similar mathematical properties such as peaks, curvatures, number and characteristics of zero-crossings etc.

The detection process can be facilitated by providing a sample library which contains pre-selected waveforms obtained from prior experiments. To this end, the disclosed method acquires heartbeat template data describing template shapes of heartbeat in the time domain. Initial experiments have shown that the patterns described by the template shapes have a high qualitative similarity, so a supply of about 15 shapes might be sufficient.

The method then continues for example with determining, based on the component analysis data and the heartbeat template data, recurrent shape data describing a recurrence of certain signal shapes in the component analysis data.

Similarity measures like two-dimensional cross correlation or convolution with a kernel obtained from the sample library, or any other similarity measure in signal analysis can be used for determining a similarity between the signal shapes described by the component analysis data and the heartbeat template data.

The sample library contained in the heartbeat template data can be parsed, and for each template shape (template signal shape or template wave form), a process as described in the following pseudo-code can be performed:

```
for each independent component channel:
    for each waveform in library:
        slide waveform over signal channel in a defined stepsize;
        calculate similarity value between waveform and signal;
        if similarity > threshold:
            mark positions in channel;
        scan for recurrence in a sensible temporal distance to the first occurrence
        (heartrate should be between 40 and 200 beats per minute, calculate
        range with sample rate)
        else
            deform/rescale waveform and repeat;
        end;
    end;
end;
```

The average of a defined number of channels with the best obtained similarity scores is used to synthesize a signal which shows the heartbeat signal as peaks, directly aligned with the acceleration measurement data. In a different approach of the disclosed method, the most dominant harmonic peak in the spectrum of the FFT (Fast Fourier Transformation) can be used as an aid in choosing the suitable step size for the algorithm described in the pseudo code example.

If no matches are found in the sample library, more calculation intensive pattern recognition algorithms (such as autocorrelation or serial correlation) must be applied. The results can be used to populate and enhance the existing waveform library. However, in an initial approach, a suitable template library combined with the FFT comparison should be sufficient.

In order to improve further us of the disclosed method by enhancing the sample library, the following exemplary steps also for part of the disclosed method:
  determining, based on the component analysis data, whether the independent component analysis of the acceleration measurement data describes, for example within a plausible frequency range, recurring, for example periodic, time domain shapes; and
  if it is determined that the independent component analysis of the acceleration measurement data describes recurring time domain shapes (i.e. wave forms), determining whether those shapes are described by the heartbeat template data; and
    if it is determined that those shapes are not described by the heartbeat template data,
      adding those shapes to the heartbeat template data.

For example, heartbeat signal data describing a time series of the heartbeat is then determined based on the recurrent shape data, in one example by evaluating the frequency of the heartbeat signal described by the synthesized signal. H Also, the harmonics of the FFT of the synthesized heartrate channel can be used to determine the heartrate. Hence, the heartbeat signal data can be determined by determining the harmonics of the frequency domain representation of the heartbeat. The process of automatic heart beat identification (determination of the heartbeat signal data) can (alternatively) be executed by utilizing a heartbeat profile library (included in the heartbeat template data) containing prior knowledge on power-spectrum density profiles of typical independent components of a heartbeat such as the documented power-law profile of heartbeat variability over multi-minute or longer time frames—and elimination criteria for typical noise-components or noise-events (e.g. sudden head motion).

In order to check whether the thus determined heart rate is valid, the disclosed method may comprise:
  determining, based on the heartbeat signal data, a frequency domain representation of the time series of the heartbeat; and
  determining, based on the frequency domain representation, whether a peak frequency described by the frequency domain presentation matches a predetermined heartrate.

The frequency domain representation is determined for example by determining a Fourier transform of the time series of the heartbeat, for example by running a fast Fourier transformation algorithm on the heartbeat signal data. For this sanity check, the FFT of the ICA channels themselves can be calculated, and a resulting occurrence of harmonic peaks in the range of the determined heartrate indicates that the algorithm produced a plausible result.

The predetermined heartrate may for example be alternatively or additionally acquired as second measurement data received from a second heartbeat sensor such as a photoplethysmography device or an electrocardiography device, and then be compared to the heartrate determined on the basis of the heartbeat signal data.

For example, the disclosed method comprises determining the heartbeat signal data by executing at least one of the following:
  determining, based on (for example in) the recurrent shape data, a single independent component;
  determining, based on (for example in) the recurrent shape data, a combination of single independent components;
  determining at least one of a convolution cross correlation of the component analysis data and the heartbeat template data.

Using ICA for separating noise from acceleration information in a periodic signal provides for the advantage of having maximum statistical independence of the individual components and thus allows finding only signal components which are due to vascular (pulse/heartbeat-induced) vibrations.

In a second aspect, the invention is directed to a computer program which, when running on processor of a computer or when loaded into the memory of a computer, causes the computer to perform the method according to any one of the preceding claims.

In a third aspect, the invention is directed to a non-transitory computer-readable program storage medium on which the program according to the second aspect is stored.

In a fourth aspect, the invention is directed to a computer, comprising a processor and a memory, wherein the program according to the second aspect is running on the processor or is loaded into the memory, or wherein the computer comprises the program storage medium according to the third aspect.

In a fifth aspect, the invention is directed to a system for determining a heartbeat signal describing the heartbeat of a patient, the system comprising:
  a) a plurality of acceleration sensors disposable on a surface of an anatomical body part of the patient and configured to generate acceleration signals for measuring an acceleration of the surface;
  b) the computer according to the fourth aspect, the computer being operatively coupled to the acceleration sensors and configured to receive information corresponding to the acceleration signals from the acceleration sensors and to acquire the acceleration measurement data based on that information.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

DEFINITIONS

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right.

The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data, for example it encompasses the meaning of "inputting" or "loading" the data to be acquired, the expression "determining data" then encompasses the meaning of "outputting" the data to be determined. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. For example, the acquiring step does not involve an invasive step which would represent a substantial physical interference with the body, requiring professional medical expertise to be carried out and entailing a substantial health risk even when carried out with the required professional care and expertise. For example, the step of acquiring data, for example determining data, does not involve a surgical step and for example does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

DESCRIPTION OF THE FIGURES

In the following, the invention is described with reference to the appended figures which represent a specific embodiment of the invention. The scope of the invention is not however limited to the specific features disclosed in the context of the figures, wherein

As shown in FIG. 1, six acceleration sensor embodied by accelerometers 2 are disposed on the surface of an anatomical body part embodied by a patient's head 1. The accelerometers 2 are distributed such that four of them have hair-contact (top, left, right and back pods) and two of them have skin contact (left and right forehead pods). Additionally, one omnidirectional Sound Pressure Level Sensor (SPL) is included in the top pod, and one PPG sensor for generating a gate signal (as the second measurement data) is disposed between the forehead acceleration sensors 2.

The acceleration sensors are configured to measure vibrations (specifically, vibrations, due to a blood pulse in the cranial vasculature) on the surface of the head 1 and to transmit corresponding signals via data transmission connections 4 (such as a wireless connection or cables) to a computer 3 comprising a digital electronic processor and a memory for processing the signals in accordance with the disclosed method or computer program, respectively.

Figure 1A:
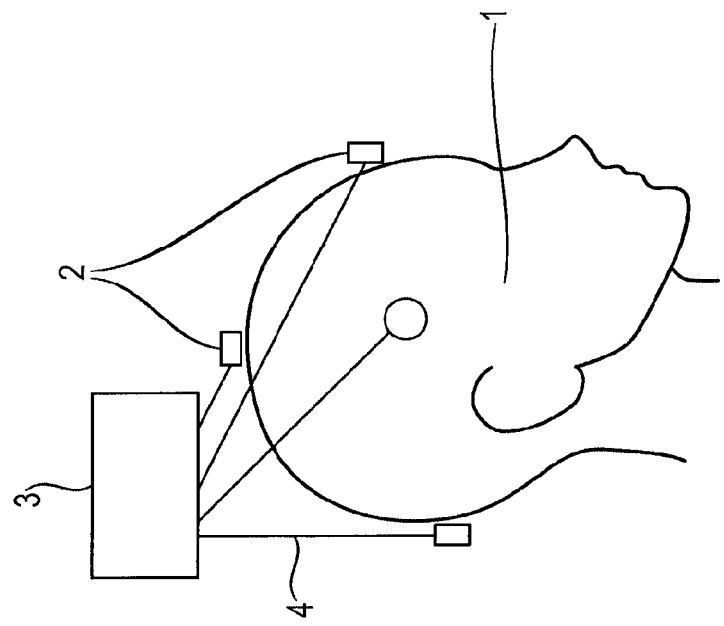
FIG. 1a illustrates a frontal view of a system for determining a heartbeat signal describing the heartbeat of a patient, when the system is attached to a patient's head.
Figure 1B:
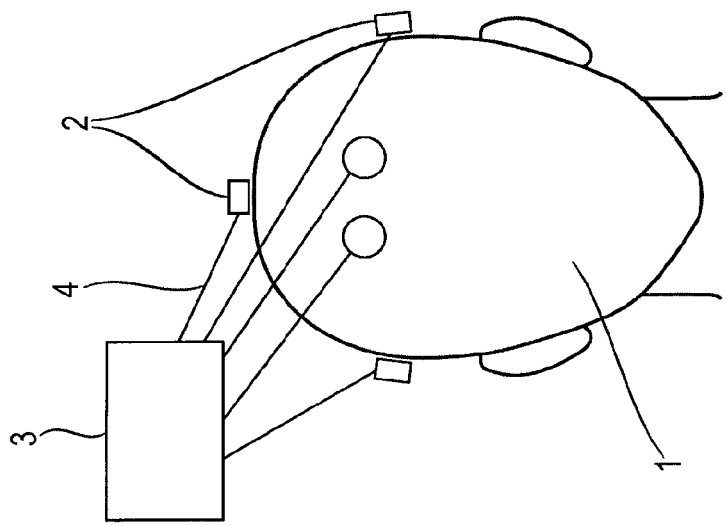
FIG. 1b illustrates a lateral view of a system for determining a heartbeat signal describing the heartbeat of a patient, when the system is attached to a patient's head.
Figure 2:
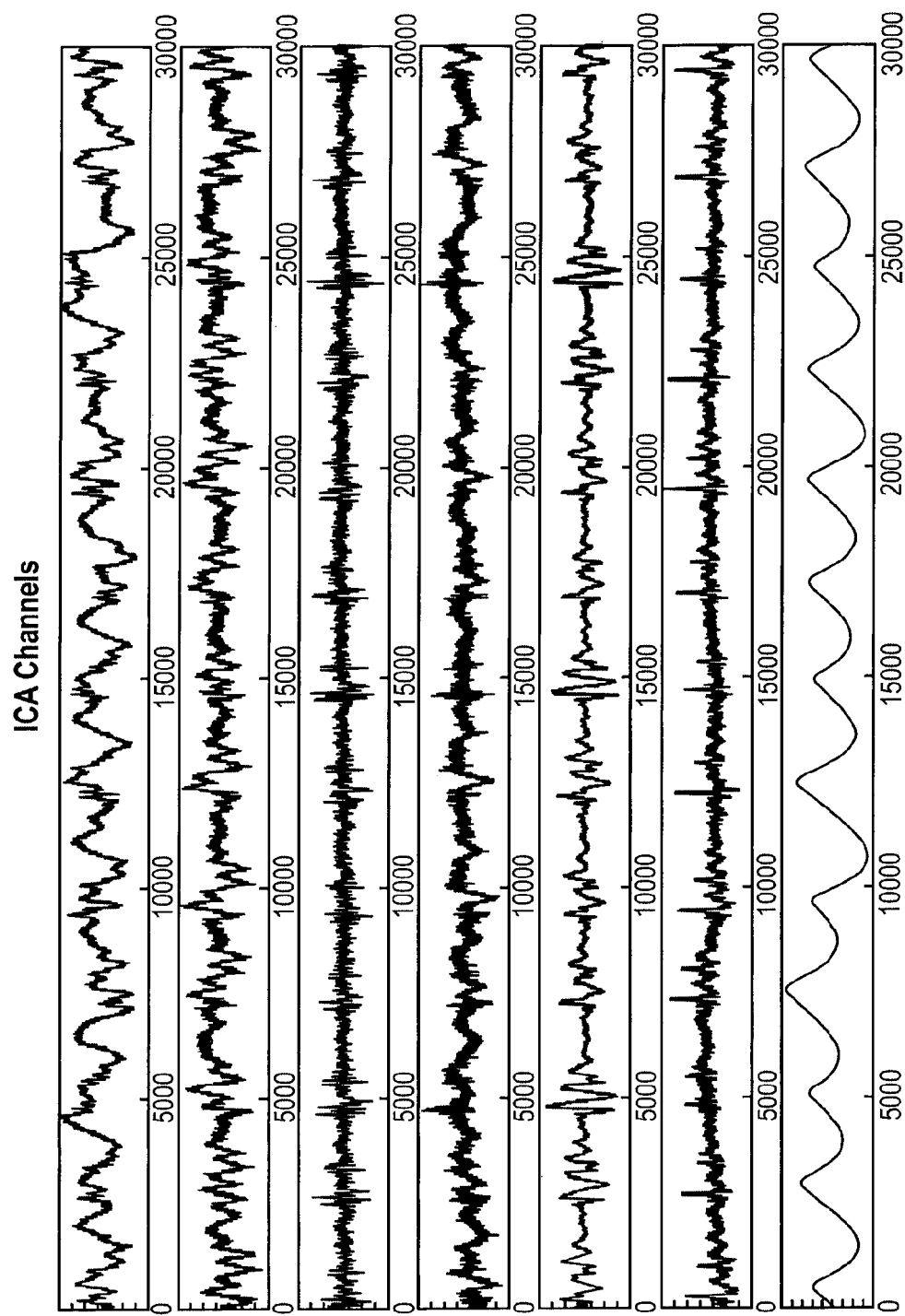
FIG. 2 shows an example of the six acceleration components extracted from a 30,000-sample point batch of the six accelerometers and the heartbeat signal recorded by a PPG sensor.
Figure 3:
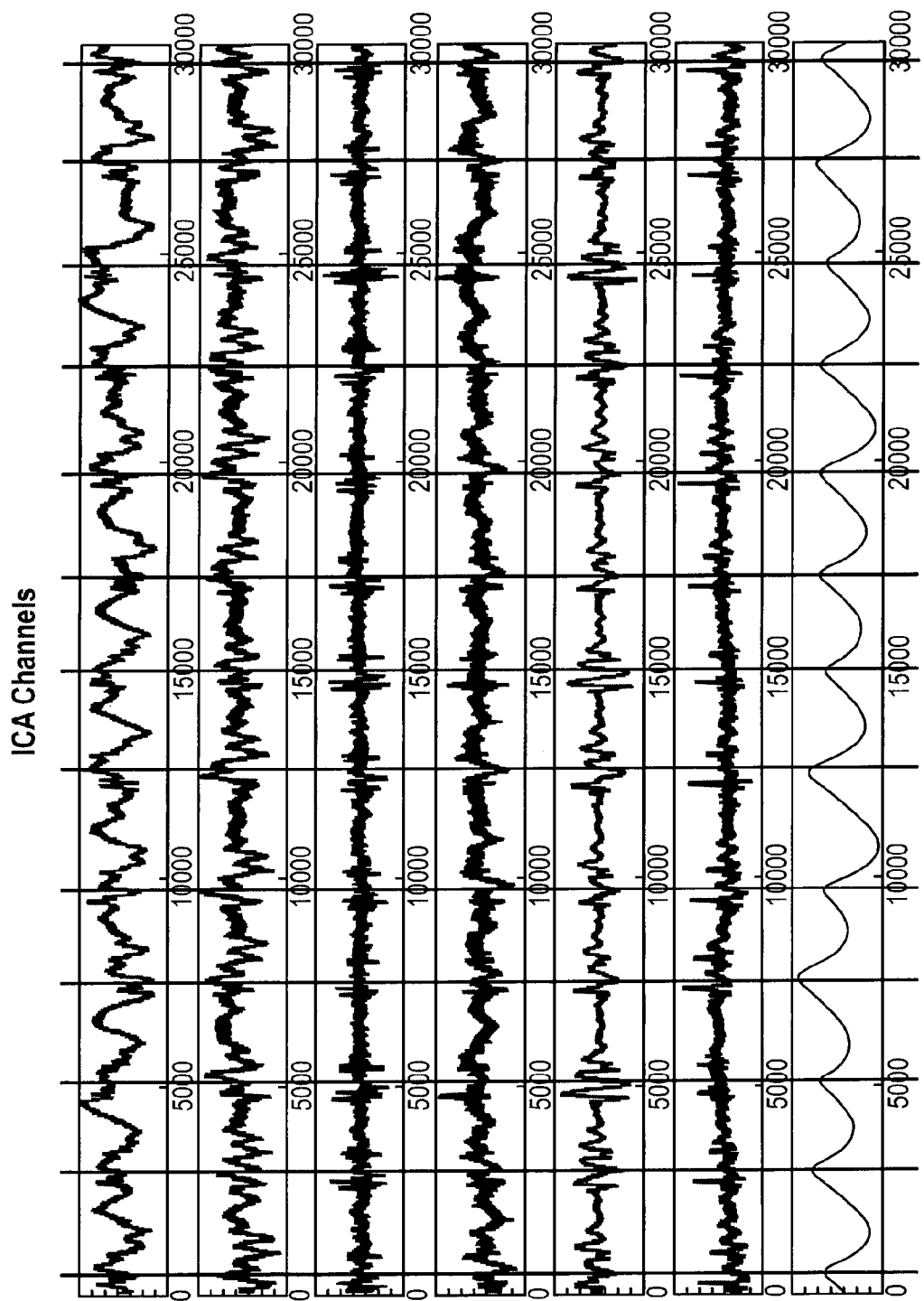
FIG. 3 shows a matching of the acceleration signals to a heartbeat signal obtained from an additional PPG sensor.

FIG. 2 is a plot of component analysis data obtained by performing ICA of acceleration measurement data received from the six acceleration sensors 2 (upper six time series, labelled "ICA Channels", corresponding to directional components of the measured acceleration), and further shows a plot of the gate signal (lowermost time series, labelled "Gate"). FIG. 3 shows how the phases of the acceleration channels during heartbeat are determined by matching them with the heartbeat indicated by the gate signals.

Figure 4:
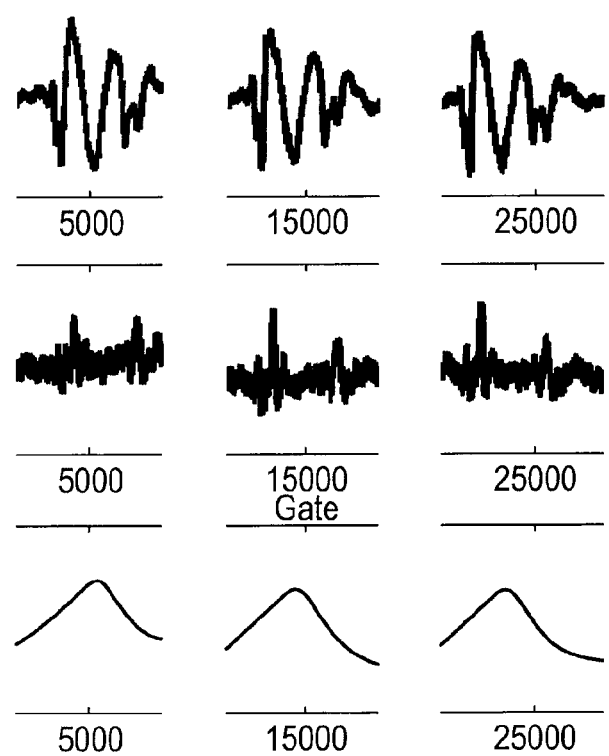
FIG. 4 shows the alignment of the heartbeat signal obtained by a PPG sensor (lowest row) with the independent components of a sample library (upper two rows) which contains predetermined waveforms obtained from prior experiments.

FIG. 4 shows how suitable waveforms (upper two rows) may be obtained from a sample library which match (to a predetermined degree) pulse signals obtained from the PPG sensor (lowermost row). The waveforms from the sample library may be compared to the component analysis data in order to determine the heartbeat signal data. Thereby, the PPG signal is not necessary for determining the heartbeat signal data, which may be obtained solely by comparison with the waveforms contained in the sample library (corresponding to the heartbeat template data).

Figure 5:
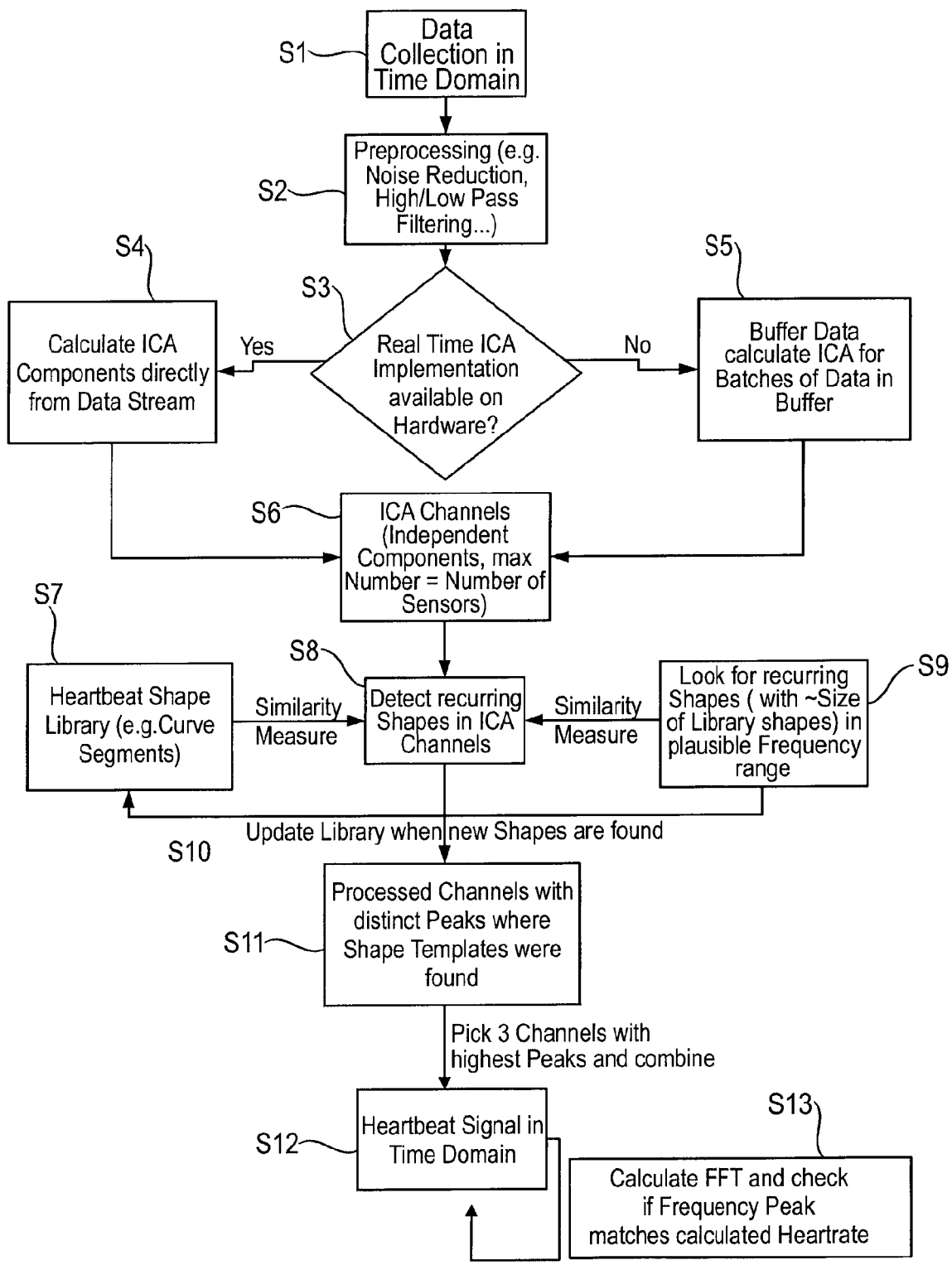
FIG. 5 shows a detailed flowchart of the method described above.

FIG. 5 contains a flowchart for illustrating execution of the disclosed method. In step S1, the acceleration measurement data is collected by the acceleration sensors 2 in the time domain. An optional step 2 encompasses preprocessing of the acceleration measurement data for noise reduction, for example by high pass or low pass filtering. Subsequent step S3 is directed to determining whether a real-time independent component analysis is possible with the used hardware. If step S3 results in that this is possible, the ICA components are calculated in step S4 directly from the data stream received from the acceleration sensors 2. If step S5 results in the negative, the data received from the acceleration sensors 2 are buffered and the ICA is calculated for batches of the data stored in the buffer (step S5). The ICA is determined by conducting ICA on the (if applicable, preprocessed) acceleration measurement data as explained above. The ICA serves to obtain the independent components as ICA channels contained in the component analysis data in step S6. The result is searched in step S8 for shapes recurring in each ICA channel. This is done by comparing (i.e. determining a similarity measure such as a cross-correlation) between e.g. curve segments contained in a predetermined heartbeat shape library (the corresponding heartbeat template data being acquired in step S7). Optionally, the heartbeat shape library can be enhanced by looking, in the component analysis data, for recurring shapes (having for example about the size of the shapes contained in the heartbeat shape library) in step S9 and, if shapes are found which are not contained in the heartbeat shape library, adding those shapes to the heartbeat library in optional step S10. Step S11 continues with determining channels with distinct peaks for which template shapes were found in step S8, and picking the three channels having the highest peaks and combining them (for example by applying a cross-correlation or averaging algorithm) to determine the heartbeat signal data describing the heartbeat signal in the time domain. Optionally, the frequency spectrum of the heartbeat signal can be determined in step S13 by subjecting it to (Fast) Fourier Transform ((F)FT). The result of this can be compared to a calculated heartrate (which may be acquired for example as the above-described second measurement data) in order to determine whether the frequency peak of the heartrate signal matches the calculated heartrate. This serves validation of the heartrate signal.

The disclosed method provides a means of obtaining the subject's heart-rate solely from accelerometer/vibration data. This means that an additional sensor/modality for registering the subject's heart-rate is no longer necessary, reducing cost and complexity of the system, while facilitating the use of the system in the daily workflow (no ECG electrodes have to be attached, and no time is wasted on establishing sufficient skin contact for a valid PPG signal, warming up the skin, attaching a separate earlobe PPG sensor).

If another modality for monitoring the heart-rate is present (such as ECG or PPG), the heart-rate information obtained directly from the acceleration measurement data can provide a means of estimating the temporal offset between the registration of a heartbeat by one of the additional sensors and the arrival of the actual blood pulse in the cerebral vasculature, providing a more exact basis for synchronization and averaging of acceleration data measured in a multitude of heartbeats.

The heartbeat signal data serves as a basis for noise removal from the acceleration measurement data, for example by synchronous averaging the acceleration measurement data over a predetermined number of (for example, forty) heartbeats. Furthermore, the heartbeat signal can serve for elasticity-based tomography of the anatomical body part which may serve to generate tomographic images. Such images can then be output on a graphical image output device such as a computer monitor.

The invention claimed is:

1. A system for determining a heartbeat signal describing the heartbeat of a patient, the system comprising:
a plurality of acceleration sensors disposable on a surface of an anatomical body part of the patient and configured to generate acceleration signals for measuring an acceleration of the surface;
at least one computer being operatively coupled to the acceleration sensors and configured to receive information corresponding to the acceleration signals from the acceleration sensors and to acquire acceleration measurement data based on that information,
wherein the at least one computer comprises at least one processor configured to execute computer-executable instructions for a method for determining a heartbeat signal describing the heartbeat of a patient in the time domain, the instructions, when executed, configure the at least one processor to:
acquire, at the at least one processor, acceleration measurement data describing an acceleration in the time domain of an anatomical body part measured on an external surface of the anatomical body part;
determine, by the at least one processor, component analysis data describing a result of an independent component analysis in the time domain of the acceleration measurement data;
acquire, at the at least one processor, heartbeat template data describing template shapes of heartbeat in the time domain;
determine, by the at least one processor and based on the component analysis data and the heartbeat template data, recurrent shape data describing a recurrence of certain signal shapes in the component analysis data; and
determine, by the at least one processor and based on the recurrent shape data, heartbeat signal data describing a time series of the heartbeat.

2. A computer-implemented method for determining a heartbeat signal describing the heartbeat of a patient in the time domain, the method comprising:
a) obtaining, from a plurality of acceleration sensors by at least one processor, acceleration measurement data describing an acceleration in the time domain of an anatomical body part measured on an external surface of the anatomical body part;
b) determining, by the at least one processor, component analysis data describing a result of an independent component analysis in the time domain of the acceleration measurement data;
c) acquiring, at the at least one processor, heartbeat template data describing template shapes of heartbeat in the time domain;
d) determining, by the at least one processor and based on the component analysis data and the heartbeat template data, recurrent shape data describing a recurrence of certain signal shapes in the component analysis data;
e) determining, by the at least one processor and based on the recurrent shape data, heartbeat signal data describing a time series of the heartbeat.

3. The method according to claim 2, wherein the anatomical body part comprises the head.

4. The method according to claim 2, comprising
preprocessing, by the at least one processor, the acceleration measurement data for at least one of noise reduction, low pass filtering and high pass filtering.

5. The method according to claim 2, comprising
determining, by the at least one processor, whether a real-time independent component analysis on the acceleration measurement data is possible, and
if determined that the real-time independent component analysis is possible, determining, by the at least one processor, the component analysis data from a stream of the acceleration measurement data; and
if determined that the real-time independent component analysis is not possible, buffering, by the at least one processor, the acceleration measurement data and determining, by the at least one processor, the component analysis data by conducting the independent component analysis on at least one batch of the buffered acceleration measurement data.

6. The method according to claim 2, comprising
determining, by the at least one processor and based on the component analysis data, whether the independent component analysis of the acceleration measurement data describes recurring time domain shapes; and
if determined that the independent component analysis of the acceleration measurement data describes recurring time domain shapes,
determining, by the at least one processor, whether those shapes are described by the heartbeat template data; and
if determined that those shapes are not described by the heartbeat template data,
adding, by the at least one processor, those shapes to the heartbeat template data.

7. The method according to claim 2, comprising
performing the independent component analysis by running, by the at least one processor, a fast independent component analysis algorithm on the acceleration measurement data.

8. The method according to claim 2, comprising
determining, by the at least one processor and based on the heartbeat signal data, a frequency domain representation of the time series of the heartbeat; and
determining, by the at least one processor and based on the frequency domain representation, whether a peak frequency described by the frequency domain representation matches a predetermined heartrate.

9. The method according to claim 8, wherein the frequency domain representation is determined by determining a Fourier transform of the time series of the heartbeat.

10. The method according to claim 8, wherein the predetermined heartrate is acquired, at the at least one processor, as second measurement data received from a second heartbeat sensor, wherein the second heartbeat sensor includes at least one of a photoplethysmography device or an electrocardiography device.

11. The method according to claim 2, wherein the heartbeat signal data is determined by executing at least one of the following:
determining, by the at least one processor and based on the recurrent shape data, a single independent component;
determining, by the at least one processor and based on the recurrent shape data, a combination of single independent components; or
determining, by the at least one processor, at least one of a convolution cross correlation of the component analysis data and the heartbeat template data.

12. The method according to claim 9, wherein the heartbeat signal data is determined by determining, by the at least one processor, the harmonics of the frequency domain representation of the heartbeat.

13. A non-transitory computer-readable program storage medium on which a program is stored which, when executed by at least one processor of at least one computer, causes the at least one computer to perform a method for determining a heartbeat signal describing the heartbeat of a patient in the time domain, the program for the method configures the at least one processor to:

obtain, from a plurality of acceleration sensors, acceleration measurement data describing an acceleration in the time domain of an anatomical body part measured on an external surface of the anatomical body part;
determine component analysis data describing a result of an independent component analysis in the time domain of the acceleration measurement data;
acquire heartbeat template data describing template shapes of heartbeat in the time domain;
determine, based on the component analysis data and the heartbeat template data, recurrent shape data describing a recurrence of certain signal shapes in the component analysis data;
determine, based on the recurrent shape data, heartbeat signal data describing a time series of the heartbeat.

14. The non-transitory computer-readable program storage medium of claim 13, wherein the program further configures the at least one processor to preprocess the acceleration measurement data prior to the independent component analysis.

15. The non-transitory computer-readable program storage medium of claim 13, wherein, to determine recurrent shape data, the program configures the at least one processor to compare a heartbeat template shape, from the heartbeat template data, to a component channel from the component analysis data.

16. The non-transitory computer-readable program storage medium of claim 15, wherein the program further configures the at least one processor to slide the heartbeat template shape over the component channel according to a predetermined step size and identify positions where a similarity value exceeds a threshold.

17. The non-transitory computer-readable program storage medium of claim 15, wherein the program further configures the at least one processor to determine recurrence of the heartbeat template shape on the component channel within an anatomical relevant distance from the identified positions.

18. The non-transitory computer-readable program storage medium of claim 15, wherein the program further configures the at least one processor to:
identify a recurring shape in at least one component channel following the independent component analysis of the acceleration measurement data;
determine whether the recurring shape is described in the heartbeat template data; and
add the recurring shape to the heartbeat template data when the recurring shape is not described.

19. The non-transitory computer-readable program storage medium of claim 15, wherein the program further configures the at least one processor to determine a heartrate from the heartbeat signal data.

20. The non-transitory computer-readable program storage medium of claim 19, wherein the program further configures the at least one processor to:
acquire second measurement data from a second heartbeat sensor; and
validate the heartrate determined from the heartbeat signal data based on the second measurement data.

* * * * *